US011439494B2

(12) United States Patent
Wu et al.

(10) Patent No.: US 11,439,494 B2
(45) Date of Patent: Sep. 13, 2022

(54) MEDICAL DEVICES

(71) Applicant: MicroVention, Inc., Aliso Viejo, CA (US)

(72) Inventors: Xinping Wu, Aliso Viejo, CA (US); Jodi Hong, Aliso Viejo, CA (US); Gregory M. Cruise, Rancho Santa Margarita, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 473 days.

(21) Appl. No.: 15/977,967

(22) Filed: May 11, 2018

(65) Prior Publication Data
US 2018/0325649 A1    Nov. 15, 2018

Related U.S. Application Data

(60) Provisional application No. 62/505,726, filed on May 12, 2017.

(51) Int. Cl.
| | |
|---|---|
| *A61F 2/06* | (2013.01) |
| *A61L 31/14* | (2006.01) |
| *A61F 2/00* | (2006.01) |
| *A61L 31/02* | (2006.01) |
| *A61L 31/10* | (2006.01) |
| *A61L 31/08* | (2006.01) |
| *A61F 2/82* | (2013.01) |

(52) U.S. Cl.
CPC .............. *A61F 2/06* (2013.01); *A61F 2/0077* (2013.01); *A61L 31/022* (2013.01); *A61L 31/10* (2013.01); *A61L 31/14* (2013.01); *A61F 2/82* (2013.01); *A61L 31/08* (2013.01); *A61L 2400/18* (2013.01)

(58) Field of Classification Search
CPC ... A61F 2/06; A61F 2/02; C08F 20/06; G01N 33/54386; C07K 14/00; C23C 16/00
See application file for complete search history.

(56) References Cited

U.S. PATENT DOCUMENTS

| | | | |
|---|---|---|---|
| 7,056,523 B1 * | 6/2006 | Claude ..................... | A61F 2/86 424/426 |
| 7,060,415 B2 | 6/2006 | Kitson et al. | |
| 7,695,775 B2 | 4/2010 | Kobrin et al. | |
| 7,910,678 B2 | 3/2011 | Pacetti | |
| 9,050,393 B2 | 6/2015 | Saffran | |
| 2003/0100694 A1 | 5/2003 | Holguin | |
| 2006/0088666 A1* | 4/2006 | Kobrin ..................... | B05D 1/60 427/569 |
| 2008/0221224 A1* | 9/2008 | Sheiko ..................... | C08F 20/56 514/789 |
| 2010/0069608 A1* | 3/2010 | Lloyd ..................... | A61L 27/54 530/324 |
| 2011/0104508 A1 | 5/2011 | Wang et al. | |
| 2014/0017772 A1* | 1/2014 | Di Matteo ................ | G03F 7/16 435/287.1 |

FOREIGN PATENT DOCUMENTS

CN    1391886 A    1/2003

OTHER PUBLICATIONS

Wang et al., Antibacterial Coatings on Titanium Surfaces: A Comparison Study Between In Vitro Single-Species and Multispecies Biofilm, Mar. 18, 2015, ACS Applied Material Interfaces, vol. 7, Issue 10, pp. 5992-6001 (Year: 2015).*
Karakoy et al., Silane surface modification for improved bioadhesion of esophogeal implants, Aug. 30, 2014, Applied Surface Sciences, vol. 311, pp. 684-689 (Year: 2014).*
Cowley et al., A Healthy Future: Platinum in medical applications. Platinum Metals Review, vol. 55, No. 2, pp. 98-107 (2011).
International Application Serial No. PCT/US2018/032431 filed on May 11, 2018.
International Search Report and Written Opinion dated Jul. 20, 2018 for International Application Serial No. PCT/US2018/032431 filed on May 11, 2018.
Tajima et al., Differential regulation of endothelial cell adhesion, spreading, and cytoskeleton on low-density polyethylene by nanotopography and surface chemistry modification induced by argon plasma treatment. Journal of biomedical Materials Research, Part A, vol. 84A, No. 3, pp. 828-836 (2007).

* cited by examiner

*Primary Examiner* — Dah-Wei D. Yuan
*Assistant Examiner* — Andrew J Bowman
(74) *Attorney, Agent, or Firm* — K&L Gates LLP; Brian J. Novak; Benjamin D. Heuberger

(57) ABSTRACT

Described are medical devices including expandable tubular bodies configured to be implanted into a lumen, wherein the outer surface of the expandable tubular bodies are coupled to a polymer(s).

15 Claims, No Drawings

MEDICAL DEVICES

CROSS REFERENCE TO RELATED APPLICATIONS

This application claims the benefit of U.S. provisional patent application No. 62/505,726, filed May 12, 2017, the entire disclosure of which is incorporated herein by reference.

FIELD

Described herein are medical devices, including stents and flow diverters, with covalently bonded polymer coatings that can reduce thrombogenicity. Methods of making and using the medical devices are also described.

SUMMARY

Described herein are medical device coatings. The device coatings can be used for any medical devices that may come into contact with tissue and/or blood. In some embodiments, the coatings can prevent or reduce thrombus formation around a device when compared to an uncoated device.

Expandable, tubular bodies, including stents and flow diverters, are widely used in the medical field to treat a variety of vascular conditions, including stenosis and dilatation or weakening of arterial walls (i.e., aneurysm). For the treatment of stenosis, a stent is inserted into the blockage of the vessel and deployed. The stent buttresses the blockage out of the lumen of the vessel, restoring blood flow. For the treatment of an intracranial aneurysm, a stent may be deployed across the neck of the aneurysm to provide support for subsequent coiling of the aneurysm. Alternatively, a flow diverter may be deployed across the neck of the aneurysm to reduce or eliminate the exposure of the aneurysm wall to blood flow.

While stents and flow diverters are widely used to successfully treat various vascular conditions, they are not without limitations. One such limitation is the requirement of antiplatelet therapy to prevent thrombosis of the stent. Currently, dual antiplatelet therapy is the standard of care. Low dose aspirin is recommended indefinitely. A P2Y12 inhibitor (i.e., clopidogrel (Plavix), prasugrel (Efient, Effient), ticagrelor (Brilinta), and cangrelor (Kengreal)) is recommended for up to 12 months post-procedure. While dual antiplatelet therapy is effective for maintaining the lumen of the stented vessel, bleeding (i.e., gastrointestinal or intracranial) complications can arise. While not frequent, these complications are associated with morbidity and mortality. As a result, efforts to reduce or eliminate dual antiplatelet therapy are being performed.

One such coating to reduce the thrombogenicity of stents is phosphorylcholine. In such an embodiment, a cobalt-chrome braided flow diverter is covalently coupled with phosphorylcholine in effort to reduce thrombogenicity. A reduction in thrombogenicity of the coated flow diverters compared to the uncoated flow diverters using the thrombogram test can be seen.

Another coating to potentially reduce the thrombogenicity of stents is heparin. In such an embodiment, a heparin coating is dip coated or spray coated over a stent in effort to reduce thrombogenicity. However, effects of the heparin coating in reducing thrombogenicity is not known.

Anti-thrombotic coatings can be performed on tubular, expandable devices as well as on a wide range of blood contacting medical devices, including tubing, catheters, cardiopulmonary bypass, and blood oxygenators. For example, a polymeric coating comprising poly(methoxyethyl acrylate) has been developed for the coating of blood gas oxygenators. This polymer is coated on every surface of the perfusion circuit to reduce thrombogenicity. However, this polymer is simply adsorbed to the surface and it suitable only for equipment that will be used for a short period of time.

Many other molecules have been evaluated for the coating of stents, flow diverters, and other blood contacting medical devices. However, a satisfactory, durable coating has not been found.

Described herein are tubular, expandable devices. These devices can be configured to be implanted in the vasculature or other body lumen. The medical device surface is coupled to a polymer that can reduce the thrombogenicity of the tubular, expandable device. In some embodiments, the coupling is through a covalent linkage.

In one embodiment, the tubular, expandable devices include of a plurality of braided filaments woven into a configuration to be implanted into a vessel. The braided filaments can be metallic. The metallic composition can include gold, silver, copper, steel, aluminum, titanium, cobalt, chromium, platinum, nickel, combinations thereof, alloys thereof such as, but not limited to nitinol (nickel-titanium), cobalt-nickel, cobalt-chromium, platinum-tungsten, and combinations thereof.

In another embodiment, the tubular, expandable devices can include a metallic tube laser cut into a configuration to be implanted into a vessel. The metallic tube may include gold, silver, copper, steel, aluminum, titanium, cobalt, chromium, platinum, nickel, combinations thereof, alloys thereof such as, but not limited to nitinol (nickel-titanium), cobalt-nickel, cobalt-chromium, platinum-tungsten, and combinations thereof.

In one embodiment, the polymer can be prepared by polymerizing an alkoxyalkyl (meth)acrylate or derivatives thereof and a second monomer containing an amine, a carboxylic acid, or a hydroxyl group. In one embodiment the second monomer is aminoethyl methacrylate, N-(3-aminopropyl) methacrylamide, combinations thereof, or derivatives thereof. In another embodiment, the second monomer is acrylic acid, methacrylic acid, combinations thereof, and derivatives thereof. In another embodiment, the second monomer is hydroxyethyl methacrylate, hydroxyethyl acrylate, hydroxypropyl acrylate, hydroxybutyl acrylate, combinations thereof, or derivatives thereof.

In other embodiments, the polymer is prepared by polymerizing tetrahydrofurfuryl acrylate or derivatives thereof and a second monomer containing an amine, a carboxylic acid, or a hydroxyl group. In one embodiment, the second monomer is aminoethyl methacrylate, N-(3-aminopropyl) methacrylamide, combinations thereof, or derivatives thereof. In another embodiment, the second monomer is acrylic acid, methacrylic acid, combinations thereof, and derivatives thereof. In another embodiment, the second monomer is hydroxyethyl methacrylate, hydroxyethyl acrylate, hydroxypropyl acrylate, hydroxybutyl acrylate, combinations thereof, or derivatives thereof.

Methods of coating an implantable medical device are also described. The methods can include activating a surface of the implantable medical device by silanization, and coupling a polymer formed from a first acrylate monomer and a second monomer containing an amine, a carboxylic acid, or a hydroxyl group to the activated surface.

In some embodiments, the methods further comprise hydroxylation of the surface using oxygen plasma.

In some embodiments, the silanization occurs through reaction with a compound having a structure

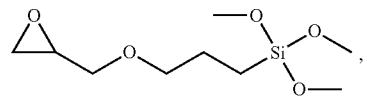

3-glycidyloxypropyltrimethoxysilane

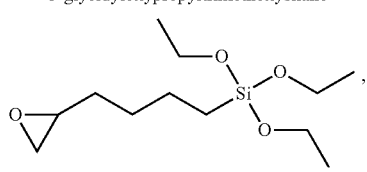

5,6-epoxyhexyltriethoxysilane

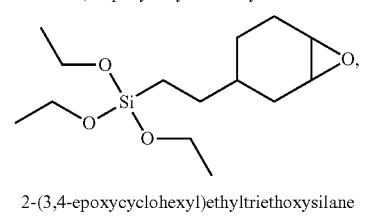

2-(3,4-epoxycyclohexyl)ethyltriethoxysilane

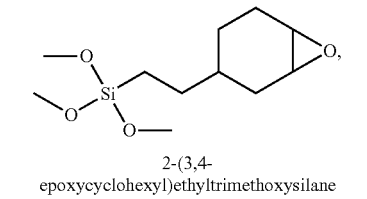

2-(3,4-epoxycyclohexyl)ethyltrimethoxysilane

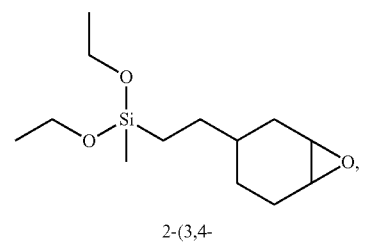

2-(3,4-epoxycyclohexyl)ethylmethyldiethoxysilane

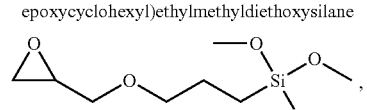

(3-glycidoxypropyl)trimethoxysilane

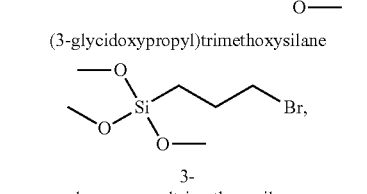

3-bromopropyltrimethoxysilane

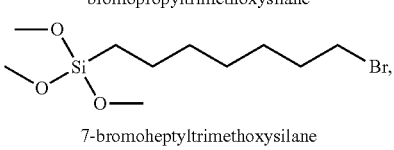

7-bromoheptyltrimethoxysilane

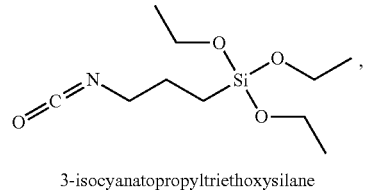

3-isocyanatopropyltriethoxysilane

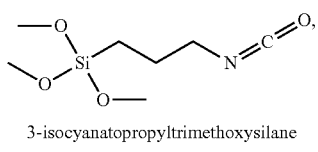

3-isocyanatopropyltrimethoxysilane

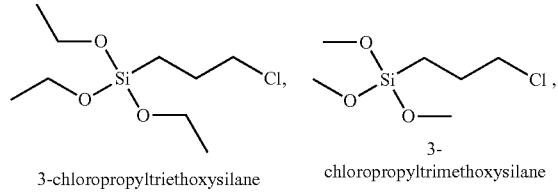

3-chloropropyltriethoxysilane    3-chloropropyltrimethoxysilane chlorophenyltriethoxysilane, chloromethyltriethoxysilane, chloromethyltrimethoxysilane,

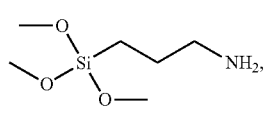

3-aminopropyltrimethoxysilane

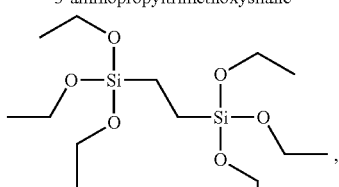

1,2-bis(trimethoxysilane)ethane

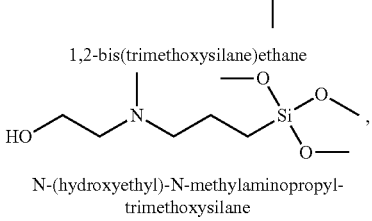

N-(hydroxyethyl)-N-methylaminopropyl-trimethoxysilane

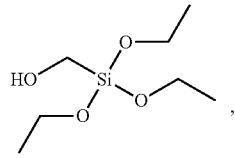

hydroxymethyltriethoxysilane

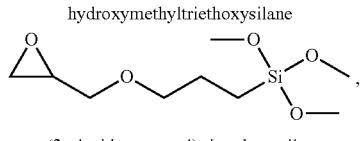

(3-glycidoxypropyl)trimethoxysilane

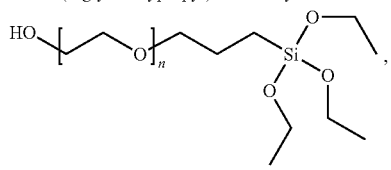

[hydroxy(polyethyleneoxy)propyl]-triethoxysilane

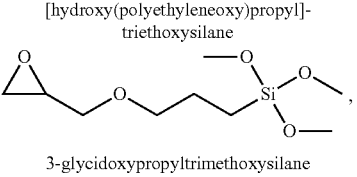

3-glycidoxypropyltrimethoxysilane

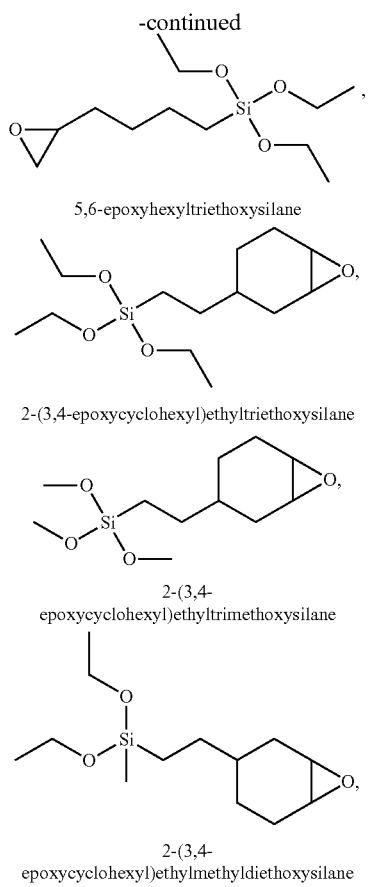

5,6-epoxyhexyltriethoxysilane 2-(3,4-epoxycyclohexyl)ethyltriethoxysilane 2-(3,4-epoxycyclohexyl)ethyltrimethoxysilane 2-(3,4-epoxycyclohexyl)ethylmethyldiethoxysilane or a combination thereof, wherein n is 1, 2, 3, 4, 5, 6, 7, 8, 9, 10, 11, 12, 13, 14, or 15.

In some embodiments, the method further includes argon plasma treatment after silanization.

In some embodiments, the first monomer is alkoxyalkyl (meth)acrylate or tetrahydrofurfuryl acrylate. In other embodiments, the second monomer is acrylic acid, methacrylic acid, hydroxyethyl methacrylate, hydroxyethyl acrylate, hydroxypropyl acrylate, hydroxybutyl acrylate, aminoethyl methacrylate, N-(3-aminopropyl) methacrylamide, a combination thereof.

DETAILED DESCRIPTION

The medical devices described herein may be any material or device that contacts blood flow, including oxygenators, artificial blood vessels, cardiopulmonary bypass machines, catheters, guidewires, stents, flow diverters, venous filters, distal protection devices, tubing, stent-grafts, and the like. In some embodiments, the medical device is a stent or flow diverter. In other embodiments, the medical device is a braided stent or flow diverter.

At least a portion of a medical device surface can be coated. In some embodiments, portions of a medical device may be masked using the herein described coatings. In some embodiments, at least about 10%, at least about 20%, at least about 30%, at least about 40%, at least about 50%, at least about 60%, at least about 70%, at least about 80%, at least about 90%, at least about 95%, or at least about 95% of the medical device surface can be coated.

The surfaces of the medical devices can be treated/coated to reduce thrombogenicity. The medical devices can include a surface treatment to reduce thrombogenicity as well as methods for application of the coatings to medical devices.

The substrate for the coating may be any suitable material, including metals, glass, polymers, ceramics, combinations thereof, and the like. In some embodiments, the substrate is a metal. While any metallic surface may be used, suitable metals can include gold, silver, copper, steel, aluminum, titanium, cobalt, chromium, platinum, nickel, alloys thereof, and combinations thereof. Suitable alloys can include nitinol (nickel-titanium), cobalt-nickel, cobalt-chromium, and platinum-tungsten. In one embodiment, the substrate is a combination of nitinol and platinum-tungsten.

The polymer of the reduced thrombogenicity coating can be prepared by polymerization of two or more monomers. The first monomer may be represented by the formulas

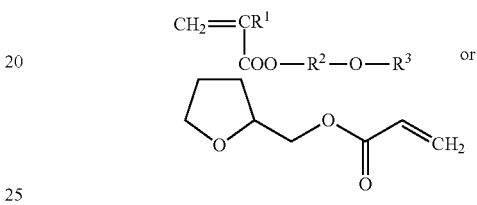

wherein $R^1$ is a hydrogen atom or methyl group, $R^2$ is an alkylene group with 1 to 4 carbons, and $R^3$ is an alkylene group with 1 to 4 carbons.

In some embodiments, a first monomer is methoxyethyl acrylate with $R^1$ is a hydrogen atom, $R^2$ is an ethyl group, and $R^3$ is a methyl group.

The second and subsequent monomers can contain a polymerizable acrylate or methacrylate as well as an amine, carboxylic acid, or hydroxyl group. Monomers containing amines can include N-(3-aminopropyl) methacrylamide, 2-aminoethyl methacrylate, N-(3-methylpyridine)acrylamide, 2-(N, N-dimethylamino)ethyl methacrylate, 2-(N, N-dimethylamino)ethyl acrylate, 2-(tert-butylamino)ethyl methacrylate, methacryloyl-L-lysine, N-(2-(4-aminophenyl)ethyl)acrylamide, N-(4-aminophenyl)acrylamide, and N-(2-(4-imidazolyl)ethyl)acrylamide, derivatives thereof, and combinations thereof. Monomers containing carboxylic acids can include acrylic acid, methacrylic acid, derivatives thereof, and combinations thereof. Monomers containing hydroxyl groups include 2-hydroxyethyl acrylate, 2-hydroxyethyl methacrylate, 2-hydroxypropyl acrylate, 4-hydroxybutyl acrylate, derivatives thereof, and combinations thereof.

In one embodiment, to prepare the polymer, the two or more monomers and an initiator are dissolved in a solvent. In general, any solvent that dissolves the two or more monomers and the initiator can be used. Due to the disparate solubility of alkoxyalkyl(meth)acrylate and the monomer containing an amine salt, judicious solvent selection may be required. Suitable solvents can include methanol/water, ethanol/water, isopropanol/water, dioxane/water, tetrahydrofuran/water, dimethylformamide/water, dimethylsulfoxide and/or water, and combinations thereof. With carboxylic acid and hydroxyl containing monomers, a wider range of solvents can be utilized, including toluene, xylene, dimethylsulfoxide, dioxane, THF, methanol, ethanol, and dimethyl formamide.

Polymerization initiators can be used to start the polymerization of the monomers in the solution. The polymerization can be initiated by reduction-oxidation, radiation, heat, or any other method known in the art. Radiation crosslinking of the monomer solution can be achieved with ultraviolet light or visible light with suitable initiators or ionizing radiation (e.g. electron beam or gamma ray) without initiators. Polymerization can be achieved by application of heat, either by conventionally heating the solution using a heat source such as a heating well, or by application of infrared light to the monomer solution.

In some embodiments, an initiator may not be used.

In one embodiment, the polymerization initiator is azobisisobutyronitrile (AIBN) or a water soluble AIBN derivatives (2,2'-azobis(2-methylpropionamidine) dihydrochloride), or 4,4'-azobis(4-cyanopentanoic acid). Other suitable initiators include N,N,N',N'-tetramethylethylenediamine, ammonium persulfate, benzoyl peroxides, and combinations thereof, including azobisisobutyronitriles. Initiator concentrations can range from about 0.25% to about 2% w/w of the mass of the monomers in solution. The polymerization reaction can be performed at elevated temperatures, such as in the range from about 65 to about 85° C. After the polymerization is completed, the polymer can be recovered by precipitation in a non-solvent and dried under vacuum.

In some embodiments, the polymers described herein can have a molecular weight of greater than about 10,000 g/mol, between about 10,000 g/mol and about 200,000 g/mol, between about 8,000 g/mol and about 200,000 g/mol, between about 100,000 g/mol and about 200,000 g/mol, between about 50,000 g/mol and about 200,000 g/mol, between about 25,000 g/mol and about 200,000 g/mol, between about 8,000 g/mol and about 100,000 g/mol, between about 10,000 g/mol and about 100,000 g/mol, between about 50,000 g/mol and about 100,000 g/mol, between about 75,000 g/mol and about 100,000 g/mol, between about 75,000 g/mol and about 200,000 g/mol, about 10,000 g/mol, about 50,000 g/mol, about 100,000 g/mol, about 150,000 g/mol, or about 200,000 g/mol.

In one embodiment, the polymer is applied to the substrate in several steps, each of which may or may not be optional. In some embodiments, the polymer is applied to the substrate in four steps. The necessity of each step is driven by the selection of the substrate.

Step 1 includes cleaning. To clean the substrate, it can be incubated in acetone, methanol, ethanol, isopropyl alcohol, water, or a combination thereof under sonication. The duration of each washing step ranges from about 1 minute to about 20 minutes. The temperature of sonication can range from about 18 to about 55° C. Following the conclusion of Step 1, the substrate moves to Step 2. In some embodiments, Step 2 immediately follows Step 1.

In some embodiments, cleaning can optionally include cleaning with soap/detergent and water.

Step 2 includes hydroxylation, a treatment to increase the number of hydroxyl groups on the surface of the substrate. The surface to be treated may be hydroxylated using a number of different oxidizers, including acids, bases, peroxides, plasma treatment, and combinations thereof.

Acids for treatment include hydrochloric acid, nitric acid, sulfuric acid, hydrofluoric acid, perchloric acid, and combinations thereof. Bases for treatment include sodium hydroxide, ammonium hydroxide, and combinations thereof. Peroxides for treatment include hydrogen peroxide, t-butyl peroxide, and combinations thereof. In one embodiment, an oxidizer is hydrogen peroxide. The oxidizer used for hydroxylation may be in concentration from about 1% to about 100%. The hydroxylation duration can range from about 0.25 hr to about 4 hr at temperatures ranging from about 18 to about 100° C. After hydroxylation, the substrate may be washed in acetone, methanol, ethanol, isopropyl alcohol, water, or combination thereof, with or without sonication. Each wash can range from about 1 minute to about 15 minutes in duration. Drying under vacuum may optionally follow washing. In one embodiment, a hydroxylation utilizes about 10% hydrogen peroxide at about 100° C. for about 45 minutes followed by about 5 min sequential washes in water, ethanol, and acetone followed by drying under vacuum.

In another embodiment oxygen plasma is used for treatment. The substrate can be exposed to oxygen plasma in a plasma treatment machine. Plasma treatment parameters can include oxygen flow, watts, pressure, and time. Oxygen flow can be from about 1-500 sccm, about 1-250 sccm, about 1-120 sccm, about 100-500 sccm, about 100-200 sccm, about 100-140 sccm, at least about 100 sccm, at least about 50 sccm, or less than about 500 sccm. Power can be from about 1-600 watts, about 1-500 watts, about 1-400 watts, about 100-600 watts, about 200-600 watts, about 400-600 watts, at least about 400 watts, at least about 500 watts, or less than about 600 watts. Pressure can be from about 120-2000 mTorr, about 200-2000 mTorr, about 200-1000 mTorr, about 300-500 mTorr, about 300-2000 mTorr, at least about 200 mTorr, at least about 300 mTorr, or less than about 2000 mTorr. Time can be from about 1-15 minutes, about 5-15 minutes, about 5-10 minutes, at least about 5 minutes, at least about 4 minutes, at least about 3 minutes, at least about 2 minutes, or at least about 1 minute. In one embodiment the oxygen flow is about 120 sccm, the power is about 500 watts, the pressure is about 400 mTorr, and the time is about 5 minutes.

Step 3 includes silanization, a treatment to bind to and introduce reactive groups to the substrate. The reactive group of the silane can include acrylate, methacrylate, aldehyde, amine, epoxy, ester, halogen, combinations thereof, and derivatives thereof. The reactive group of the silane reacts with the amine, carboxylic acid, or hydroxyl group of the second monomer of the polymer. With an amine or hydroxyl containing polymer, silanes can include

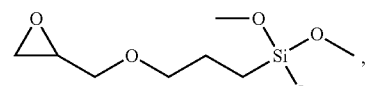

3-glycidyloxypropyltrimethoxysilane

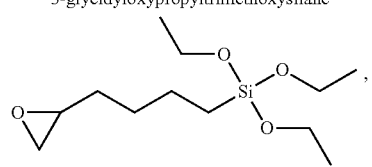

5,6-epoxyhexyltriethoxysilane

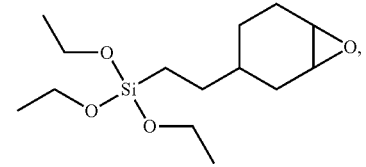

2-(3,4-epoxycyclohexyl)ethyltriethoxysilane

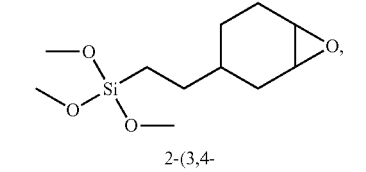

2-(3,4-epoxycyclohexyl)ethyltrimethoxysilane

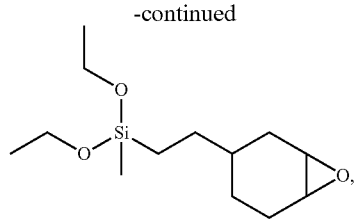

2-(3,4-epoxycyclohexyl)ethylmethyldiethoxysilane

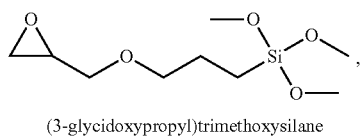

(3-glycidoxypropyl)trimethoxysilane

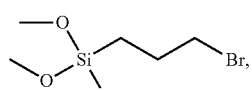

3-bromopropyltrimethoxysilane

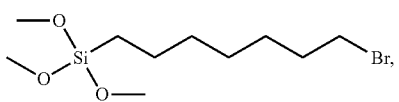

7-bromoheptyltrimethoxysilane

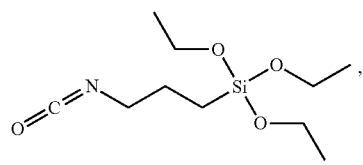

3-isocyanatopropyltriethoxysilane

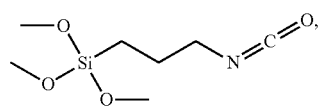

3-isocyanatopropyltrimethoxysilane

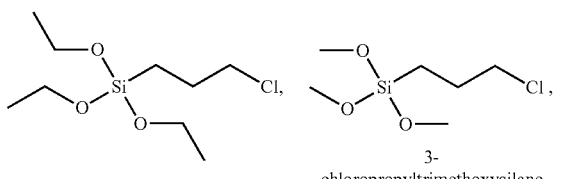

3-chloropropyltriethoxysilane    3-chloropropyltrimethoxysilane chlorophenyltriethoxysilane, chloromethyltriethoxysilane, chloromethyltrimethoxysilane, or a combination thereof.

With a carboxylic acid containing polymer, silanes can include

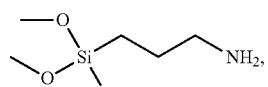

3-aminopropyltrimethoxysilane

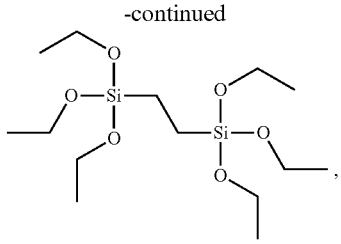

1,2-bis(trimethoxysilane)ethane

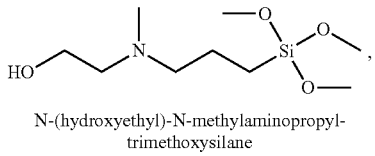

N-(hydroxyethyl)-N-methylaminopropyl-trimethoxysilane

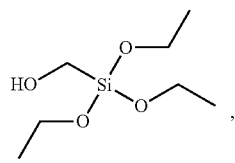

hydroxymethyltriethoxysilane

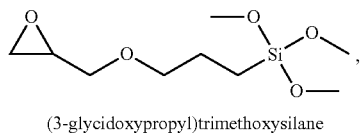

(3-glycidoxypropyl)trimethoxysilane

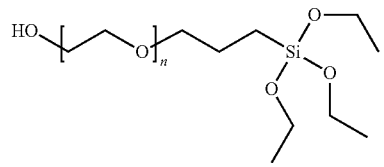

[hydroxy(polyethyleneoxy)propyl]-triethoxysilane

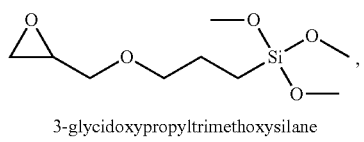

3-glycidoxypropyltrimethoxysilane

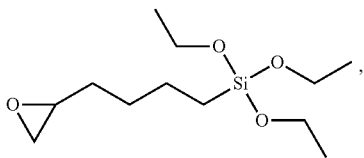

5,6-epoxyhexyltriethoxysilane

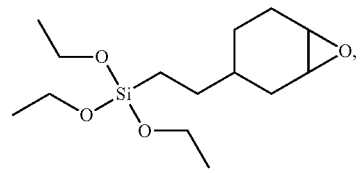

2-(3,4-epoxycyclohexyl)ethyltriethoxysilane

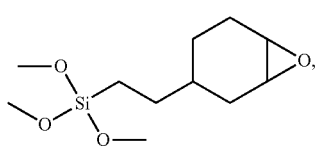

2-(3,4-epoxycyclohexyl)ethyltrimethoxysilane

-continued

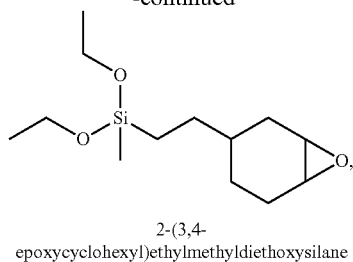

2-(3,4-epoxycyclohexyl)ethylmethyldiethoxysilane or a combination thereof. In some embodiments, n is 1, 2, 3, 4, 5, 6, 7, 8, 9, 10, 11, 12, 13, 14, or 15. In one embodiment, n is 8-12.

To perform the silanization, the selected silane is dissolved in solvent. Suitable solvents include ethanol, methanol, isopropanol, acetic acid, water, isopropanol, butanol, dimethyl formamide, dimethyl sulfoxide, ethyl acetate, toluene, chloroform, dichloromethane, and combinations thereof. In general, any solvent or mixture of solvents may be used that dissolves the silane. The solvents may be present in amounts from about 0.1% to about 99.9% by weight. Solvent percentages range from about 90% to about 99%, or about 97%. The silane may be present in amounts from about 0.1% to about 99.9% by weight. Silane percentages range from about 1% to about 10%, or about 3%. In one embodiment, a silane:solvent system is 94% ethanol, 2% water, 1% acetic acid, and 3% silane.

Following hydroxylation, the substrate may be optionally plasma treated with an argon plasma to clean the surface.

Plasma treatment parameters can include argon flow, watts, pressure, and time. Argon flow can be from about 1-500 sccm, about 1-250 sccm, about 1-120 sccm, about 100-500 sccm, about 100-200 sccm, about 100-140 sccm, at least about 100 sccm, at least about 50 sccm, or less than about 500 sccm. Power can be from about 1-500 watts, about 1-400 watts, about 1-300 watts, about 100-500 watts, about 200-500 watts, about 200-400 watts, at least about 100 watts, at least about 200 watts, or less than about 500 watts. Pressure can be from about 120-2000 mTorr, about 200-2000 mTorr, about 200-1000 mTorr, about 300-500 mTorr, about 300-2000 mTorr, at least about 200 mTorr, at least about 300 mTorr, or less than about 2000 mTorr. Time can be from about 1-15 minutes, about 5-15 minutes, about 5-10 minutes, at least about 5 minutes, at least about 4 minutes, at least about 3 minutes, at least about 2 minutes, or at least about 1 minute. In one embodiment the argon flow is about 365 sccm argon flow, the power is about 300 watts, and the pressure is about 500 mTorr for about 10 minutes.

Following plasma treatment, the substrate can be placed in the silane:solvent system. The duration of the incubation ranges from about 6 hr to 24 hr at a temperature range from about 18 to about 55° C. The silanization may optionally be performed with shaking at a rate from about 100 rpm to about 250 rpm. In one embodiment, silanization conditions are incubation for about 18 hours at room temperature with shaking at about 150 rpm.

After silanization, the substrate may be rinsed in ethanol, methanol, isopropanol, toluene, water, butanol, dimethyl formamide, dimethyl sulfoxide, ethyl acetate, chloroform, dichloromethane, and combinations thereof. In one embodiment, a rinse is ethanol. The silane layer may then be cured at temperature ranging from about 30 to about 150° C. for a duration ranging from about 5 min to 60 min. Curing conditions can be about 110° C. for about 30 min.

Step 4 includes polymer coupling, a treatment to covalently couple the polymer to the substrate. During this step, the functional group imparted to the polymer from the second or more monomer can be reacted to the functional group imparted to the substrate via the silane. In this step, the polymer can be dissolved in water, buffer, methanol, ethanol, isopropanol, butanol, dimethyl formamide, dimethyl sulfoxide, ethyl acetate, toluene, chloroform, dichloromethane, or a combination thereof. The solvent for this step can be 50% v/v ethanol:50% v/v citric buffer in water pH 7. The concentration of the polymer in the solvent can range from about 0.5% to about 95% in the solvent. In one embodiment, the concentration of the polymer in the solvent is about 1%.

The polymer solution may be applied to the substrate by dip coating, spraying, brushing, or a combination thereof. In one embodiment, the substrate may be immersed in a polymer solution for about 1 hour to about 48 hours, or in another embodiment, a duration is 18 hours. The incubation may be conducted at temperatures ranging from about 18 to about 100° C. In one embodiment, the temperature is room temperature. The coupling reaction may optionally be performed with shaking at a rate from about 100 rpm to about 250 rpm. In one embodiment, shaking conditions are about 150 rpm.

After the incubation, the substrate may optionally be rinsed ethanol, methanol, isopropanol, toluene, water, butanol, dimethyl formamide, dimethyl sulfoxide, ethyl acetate, chloroform, dichloromethane, and combinations thereof. In one embodiment, rinsing is in 50% v/v ethanol:50% v/v water. After rinsing, the substrate may be dried using heat or vacuum. The substrate may be heated at temperatures ranging from about 40° C. to about 100° C., with or without vacuum. In some embodiments, drying conditions are 40° C. under vacuum. After drying, the substrate can be sterilized and packaged.

The coated devices can be sterilized without substantially degrading the coating. After sterilization, at least about 50%, about 60%, about 70%, about 80%, about 90%, about 95% about 99% or about 100% of the coating can remain intact. In one embodiment, the sterilization method can be autoclaving, gamma irradiation, pressure sterilization, and/or steam sterilization.

The coatings described herein can prevent the growth of thrombin. In some embodiments, the coatings can reduce the amount of wet thrombin formation by about 50% to about 90%, about 70% to about 90%, about 70% to about 100%, at least about 60%, or at least about 70%. In some embodiments, the coatings can reduce the amount of thrombin formation, when measured dry, by about 60% to about 95%, about 70% to about 95%, about 70% to about 100%, at least about 70%, at least about 80%. or at least about 90%.

Example 1

Preparation of the Braided Medical Device for Silanization

First, the braided medical device is pre-cleaned using sequential incubations in acetone, ethanol, and water for 5 minutes each while sonicating. The cleaned braided medical device is incubated in a solution of 10% hydrogen peroxide in water for 45 minutes at 100° C. and then rinsed three times with water. The braided medical device is cleaned using sequential incubations in water, ethanol, and acetone for 5 minutes each while sonicating. Finally, the braided medical device is dried under vacuum for 18 hours.

Example 2

Preparation of the Braided Medical Device for Silanization Via Oxygen Plasma

First, the braided medical device is pre-cleaned using sequential incubations in acetone, ethanol, and water for 5 minutes each while sonicating. Then, the braided medical devices are transferred to a vacuum oven and dried under reduced pressure at 40° C. for 30 min. The dried braided medical devices are activated on an IoN 40 Plasma Processing System instrument, using the following parameters:

| | |
|---|---|
| Flow (Oxygen) | 120 +− 10 sccm |
| Watts | 500 watts |
| Pressure | 400 mTorr |
| Time | 5 minutes |

The activated braided medical devices are then stored in vials.

Example 3

Silanization of the Braided Medical Device

A silane solution consisting of 94% ethanol, 3% 7-bromoheptyltrimethoxy silane, 2% water, and 1% acetic acid is prepared and allowed to pre-react for 60 minutes. During the pre-reaction period, the braided medical device from Example 1 or Example 2 is plasma treated with an argon plasma (365 sccm Ar, 300 watts, 500 mTorr) for 10 minutes. Subsequently, the braided medical device is immersed in the silane solution and incubated for 18 hours at room temperature with orbital shaking at 150 revolutions per minute while protected from light. At the conclusion of the incubation, the braided medical device is rinsed with ethanol and cured at 110° C. for 30 minutes.

Example 4

Silanization of the Braided Medical Device

A mixture of silane is made using 7-bromoheptyltrimethoxysilane and 1,2-bis(trimethoxysilane)ethane at a ratio of 9:1 (v/v). The silane mixture is diluted by toluene to 5% by volume. While this silane is pre-reacting for about 60 minutes, the devices from Example 1 or Example 2 are treated with argon plasma using the same conditions as in Example 3. Subsequently, the braided medical device is immersed in the silane solution and incubated for 18 hours at 70° C. At the conclusion of the incubation, the braided medical device is rinsed with toluene and cured at 110° C. for 30 minutes.

Example 5

Preparation of Copolymer of Poly(2-Methoxyethyl Acrylate)-co-Poly[(3-Aminopropyl)Methacrylamide Hydrochloride]

To a mixture of 40 mL water and 40 mL methanol, 40 g of 2-methoxyethylacrylate, 4 g of 3-aminopropyl methacrylate hydrochloride, and 440 mg of 4,4'-azobis(4-cyanovaleric acid) are dissolved. Polymerization occurs over 4 hours at 80° C. The copolymer is recovered by precipitation in a mixture of isopropanol/hexanes (500 mL:500 mL). The copolymer is re-dissolved in a mixture of 80 mL tetrahydrofuran and 20 mL ethanol and re-precipitated in a mixture of isopropanol:hexanes (400 mL:600 mL). The copolymer is re-dissolved in a mixture of mL tetrahydrofuran and 20 mL ethanol and reprecipitated in a mixture of isopropanol:hexanes (300 mL:700 mL) and dried under vacuum. The copolymer is a white, foamy solid.

Example 6

Preparation of Copolymer of Poly(Tetrahydrofuryl Acrylate)-co-Poly[(3-Aminopropyl)Methacrylamide Hydrochloride]

To a mixture of 40 mL water and 40 mL methanol, 40 g of tetrahydrofurfuryl acrylate, 4 g of 3-aminopropyl methacrylate hydrochloride, and 440 mg of 4,4'-azobis(4-cyanovaleric acid) are dissolved. Polymerization occurs over 20 hours at 65° C. The copolymer is recovered by precipitation in a mixture of isopropanol:hexanes (500 mL:500 mL). The copolymer is re-dissolved in 100 mL tetrahydrofuran and re-precipitated in a mixture of isopropanol:hexanes (400 mL:600 mL). The copolymer is re-dissolved in 100 mL tetrahydrofuran and re-precipitated in a mixture of isopropanol:hexanes (300 mL:700 mL). The copolymer is redissolved in 100 mL tetrahydrofuran and reprecipitated in a mixture of isopropanol:hexanes (200 mL:800 mL). Finally, the copolymer is stirred in 1 L of hexane for 1 hour and dried under vacuum. The copolymer is a slightly orange, foamy solid.

Example 7

Preparation of the Coated, Braided Medical Device using Copolymer of Poly(2-Methoxyethyl Acrylate)-co-Poly[(3-Aminopropyl)Methacrylamide Hydrochloride]

The copolymer of Example 5 is dissolved in 50%/50% of ethanol/citric buffer 7.0 pH (v/v) at a final concentration of 10 mg/mL. The braided medical device of Example 3 is placed into a vial containing the copolymer solution and incubated for 18 hours at room temperature on the orbital shaker at 150 rpm. After incubation, the device is rinsed with 50%/50% ethanol/water and cured at 40° C. for 30 minutes under vacuum.

Example 8

Evaluation of the Coated, Braided Medical Device Using the Chandler Loop Model

PVC tubing (4 mm inner diameter and 6 mm outer diameter, 54.86 cm length) is measured and cut to fit on the cradle of the Chandler loop instrument (Industriedesign, Neuffen, Germany). A single pre-weighed coated, braided medical device (4.5 mm×2 cm) is deployed into the tubing. Bovine blood is freshly collected from a local slaughterhouse and heparinized at 1 U/mL. The activation clotting time (ACT) is adjusted to be between 150 and 250 seconds with protamine, if necessary. The tubing was filled with blood and the tubing is sealed with a connector. The loop is fit onto a polycarbonate stabilization disk, which is then fixed onto the Chandler Loop instrument. The loops are rotated for 2 hours at a shear rate of 300 s-1 at 37° C.

The assemblies are then taken out of the Chandler loop instrument and the blood is drained into PTFE beakers. The ACT of the drained blood is determined. The tubing is thoroughly rinsed with PBS three times to remove any residual blood. The tubing is longitudinally cut with a razor blade and the braided medical device is retrieved and photographed. The stent is weighed (wet weight) and then dried at 37° C. until the weight is constant (dry weight). The table below summarizes the results from the Chandler loop experimentation.

|  | THROMBUS WET WEIGHT (mg) | THROMBUS DRY WEIGHT (mg) |
|---|---|---|
| Uncoated Control | 53.9 | 5.7 |
| Example 7 | 12 | 0.5 |

The coating of Example 7 dramatically reduced the weight of the wet thrombus and dry thrombus.

Example 9

Evaluation of the Coated, Braided Medical Device Using X-Ray Photoelectron Spectroscopy The struts of the braided medical device are analyzed using x-ray photoelectron spectroscopy to determine elemental composition. The results are summarized in the table below.

| Samples | C | N | O | Na | Si | Ti | Ni | Br |
|---|---|---|---|---|---|---|---|---|
| Uncoated | 18.2 | 1.3 | 52.3 | — | — | 20.0 | 5.3 | — |
| Example 3 | 39.4 | 1.4 | 34.1 | — | 5.1 | 2.9 | 12.0 | 5.0 |
| Example 7 | 66.4 | 0.7 | 23.2 | 0.2 | 6.0 | 1.1 | 1.4 | 1.0 |

XPS detected no silicon or bromine on the surface of the uncoated braided medical device. The Example 3 braided medical devices had significant silicon and bromine, indicating success silanization. The Example 7 braided medical devices no longer had a ratio of Br to Si close to 1:1, indicating that the bromine has been largely displaced and the coupling reaction is successful.

Example 10

Evaluation of the Coated Medical Device Using Thrombogram

Thrombogram is performed on a Thrombinoscope instrument (Thrombinoscope B.V., Maastricht, Netherlands) in accordance with the manual. On a 96-well plate, the negative controls, test articles, and thrombin calibrator are arrayed with 9 replicates per group. Platelet-poor plasma (PPP, 240 µL) is added to all the wells and PPP-reagent (60 µL) is added to the negative control and test articles. After the FluCa solution has been added to the instrument, the start button is pressed and the 96 well plate was inserted into the instrument, starting the 10 minute incubation. At the conclusion of the incubation, the results are processed and reported. The results are summarized below.

| | Normalized per Uncoated Medical Device | | | |
|---|---|---|---|---|
| | Peak (nm) | Peak StdDev (nm) | ttPeak (min) | ttPeak StdDev (min) |
| Negative control | 186.5 | 21.6 | 29.6 | 3.1 |
| Uncoated Control | 597.2 | 73.9 | 9.5 | 0.4 |
| Example 7 | 176.0 | 41.1 | 26.7 | 2.5 |

The thrombogram of Example 7 showed equivalent results to the negative control, indicating that the coating resisted thrombin formation.

Example 11

Evaluation of the Coated, Braided Medical Device Using Blood Loop

The Example 7 braided medical devices are packaged into a delivery system and sterilized with E-beam. PVC tubing inner-lined with X-coating (OD=5/16", ID=3/16", Terumo, Japan) is cut into 140 cm length. The tubing is filled with saline and three identical devices are deployed into the tubing. Saline is then replaced with ovine blood (heparinized at 1 U/mL), and the ACT of the blood is between 150 to 250 seconds. To begin the test, the tubing is closed with tubing connector into a loop and loaded onto a peristaltic pump. While incubating the loop in a heating chamber, blood is circulated inside the loop at 273 s-1 for 2 hours±30 min. At the end of the incubation, blood is drained from each loop and the ACT is measured. The full length of the tubing is rinsed with saline. The stent is cut out of the tubing, weighed (wet weight), and then dried at 37° C. until the weight is constant (dry weight). The table below summarizes the results from the Chandler loop experimentation.

| Device | Replica | Wet Thrombus (mg) | Dry Thrombus (mg) |
|---|---|---|---|
| Uncoated Control | 1 | 64.814 | 11.014 |
| | 2 | 70.906 | 11.406 |
| | 3 | 56.284 | 11.284 |
| A | 1 | 21.59 | 1.790 |
| | 2 | 28.866 | 4.466 |
| | 3 | 13.882 | 2.082 |

The coating of Example 7 dramatically reduced the weight of the wet thrombus and dry thrombus.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible.

Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method of coating an implantable medical device, the method comprising:
    activating a surface of the implantable medical device by silanization with a silane, wherein the silane includes a reactive group selected from an acrylate, methacrylate, aldehyde, epoxy, ester, or a combination thereof, and coupling a polymer formed from a first acrylate monomer and a second monomer containing an amine, a carboxylic acid, or a hydroxyl group to the reactive group of the activated surface, wherein the first monomer is alkoxyalkyl (meth)acrylate, tetrahydrofurfuryl acrylate, or

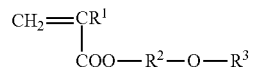

wherein
$R^1$ is hydrogen,
$R^2$ is an alkylene group with 1 to 4 carbons, and
$R^3$ is an alkyl group with 1 to 4 carbons.

2. The method of claim 1 further comprising hydroxylation of the surface using oxygen plasma.

3. The method of claim 2, wherein the oxygen plasma is applied by an oxygen flow of about 120 sccm, a power of about 500 watts, a pressure of about 400 mTorr, a time of about 5 minutes, or a combination thereof.

4. The method of claim 1, wherein silanization occurs through reaction with a silane selected from:

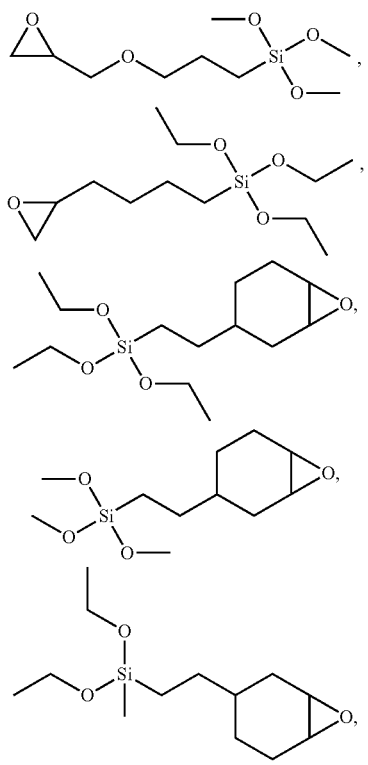

or a combination thereof.

5. The method of claim 4, wherein n is 8-12.

6. The method of claim 1 further comprising argon plasma treatment after silanization.

7. The method of claim 6, wherein the argon plasma is applied by an argon flow of about 365 sccm, a power of about 300 watts, a pressure of about 500 mTorr, a time of about 10 minutes, or a combination thereof.

8. The method of claim 1, wherein the coupling is by dip coating, spraying, brushing, or a combination thereof.

9. The method of claim 1, wherein the first monomer is tetrahydrofurfuryl acrylate.

10. The method of claim 1, wherein the second monomer is acrylic acid, methacrylic acid, hydroxyethyl methacrylate, hydroxyethyl acrylate, hydroxypropyl acrylate, hydroxybutyl acrylate, aminoethyl methacrylate, aminopropyl methacrylamide, a combination thereof.

11. The method of claim 1, wherein the silane includes an epoxy reactive group.

12. The method of claim 1, wherein the first monomer is alkoxyalkyl (meth)acrylate.

13. The method of claim 1, wherein silanization occurs through reaction with a silane selected from:

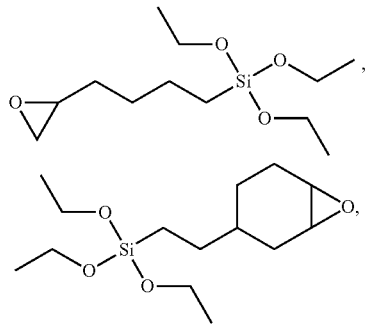

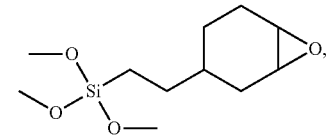

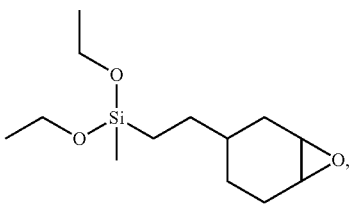

or a combination thereof.

14. The method of claim 1, wherein the second monomer is hydroxybutyl acrylate, aminopropyl methacrylamide, or a combination thereof.

15. The method of claim 1, wherein the first monomer is methoxyethyl acrylate.

* * * * *